(12) United States Patent
Käshammer et al.

(10) Patent No.: US 6,191,320 B1
(45) Date of Patent: Feb. 20, 2001

(54) FINISHING OF NEOPENTYL GLYCOL

(75) Inventors: Stefan Käshammer, Schifferstadt; Andreas Klein, Mannheim, both of (DE); Charles L. Smith, Freeport, TX (US); Winfried Müller, Mannheim (DE)

(73) Assignee: BASF Aktiengesellchaft, Ludwigshafen (DE)

( * ) Notice: Under 35 U.S.C. 154(b), the term of this patent shall be extended for 0 days.

(21) Appl. No.: 09/537,711

(22) Filed: Mar. 30, 2000

(51) Int. Cl.[7] ............................ C07C 29/74; C07C 29/76; C07C 29/78
(52) U.S. Cl. .............................................. 568/853; 568/854
(58) Field of Search ....................................... 568/853, 854

(56) References Cited

U.S. PATENT DOCUMENTS

| | | | |
|---|---|---|---|
| 4,435,603 | * | 3/1984 | Cornils et al. .................. 568/701 |
| 4,769,200 | * | 9/1988 | Hupfer et al. ................... 264/163 |

* cited by examiner

*Primary Examiner*—Peter O'Sullivan
(74) *Attorney, Agent, or Firm*—Keil & Weinkauf

(57) ABSTRACT

In a process for finishing neopentyl glycol by cooling, crystallizing and comminuting a neopentyl glycol melt and subsequent packing of the resulting neopentyl glycol particles in storage or transport containers, the melt is cooled at the commencement of cooling for at least 1/10 minutes without use of a coolant or with use of a coolant having a temperature in the range from 50 to 120° C. and the product is packed at a temperature below 30° C.

9 Claims, No Drawings

FINISHING OF NEOPENTYL GLYCOL

The present invention relates to a process for finishing neopentyl glycol by cooling, crystallizing and comminuting a neopentyl glycol melt and subsequently packing the resulting neopentyl glycol particles in storage or transport containers.

Neopentyl glycol (2,2-dimethylpropane-1,3-diol, abbreviation: NPG) is an industrially important product which is used, in particular, for producing polyesters and polyurethanes. The industrial synthesis of NPG starts out from isobutyraldehyde and formaldehyde with subsequent catalytic hydrogenation, cf. Ullmann's Encyclopedia of Chemistry, 6th Edition, Electronic Release 1998, Chapter Alcohols, Polyhydric, 2-diols, 2.2.1 Neopentyl glycol.

Solid NPG is marketed in the form of flakes. Such flakes can be produced by solidifying molten NPG by means of a flaking roll or a crystallizing belt or cooling belt. Such procedures are described, for example, in Ullmann's Encyclopedia of Industrial Chemistry, 5th Edition, Vol B2, chapter 3, pages 29–31. NPG finished in the form of flakes is sold commercially packed in, for example, sacks. Big Bags containing typically 500 kg are frequently used.

It is known that solid NPG in the form of flakes can cake during storage, as a result of which the ability of the product to flow is greatly impaired. This makes it more difficult to handle the product, in particular to empty the sacks or Big Bags. One of the causes of caking is the presence of two different crystal modifications of NPG in the solid. This effect is described in DE-A-33 47 405. It is reported that the transformation temperatures of the thermodynamically unstable modification into the thermodynamically stable form and vice versa are 42° C. or 33° C. on supercooling. The high-temperature form, which is thermodynamically stable above about 40° C., is soft and sticky. It can be supercooled down to 33° C., in particular when very pure NPG is supercooled. At this temperature, a phase transformation into the low-temperature form occurs. This solid-solid phase transformation liberates a large amount of heat. This heat evolution together with the pressure resulting from storage of sacks stacked on top of one another is responsible for caking.

The customary way of avoiding caking of solids is to add anticaking agents.

According to DE-A-33 47 405, further diols as impurities are deliberately mixed into the NPG in order to prevent caking.

DE-A-30 10 138 proposes the use of tertiary amines for this purpose.

The use of further additives for preventing caking has also been described in the past.

Another approach is followed by DE-A-35 22 359. Here, NPG is processed in a twin-screw extruder and is then extruded through a constricted passage into a low-pressure zone, cooled and broken up into particles. The constricted passage is heated, as a result of which individual crystals passing along the wall of the passage are melted to form a film which, after solidification, forms a solid jacket around the compacted crystalline material. As a result, dust-free granules having a smooth surface are obtained.

The above process requires a high outlay in terms of apparatus. The previously described processes have the disadvantage that one or more impurities have to be added. This requires an additional costly process step, since exact metering and mixing of these components into the molten NPG has to be ensured. In addition, the impurities frequently interfere in applications having high purity requirements.

It is an object of the present invention to provide a process for finishing neopentyl glycol (NPG) which avoids the disadvantages of the known processes and gives solid NPG in a form that prevents caking during storage and transport. No anticaking agents should be added.

We have found that this object is achieved by a process for finishing neopentyl glycol by cooling, crystallizing and comminuting a neopentyl glycol melt and subsequently packing the resulting neopentyl glycol particles in storage or transport containers, which process comprises cooling the melt at the commencement of cooling for at least 1/10 minutes without use of a coolant or with the use of a coolant having a temperature in the range from 50 to 120° C. and packing the product at a temperature below 30° C.

According to the present invention, it has been found that slow cooling to a temperature below 30° C. enables molten NPG to be converted into storage-stable particles such as pellets or flakes.

The slow cooling is achieved by cooling the melt at the commencement of cooling for at least 1/10 minutes, preferably at least one minute, particularly preferably at least two minutes, in particular at least three minutes, without the use of a coolant or with use of a coolant having a temperature in the range from 50 to 120° C., preferably from 60 to 110° C. If no coolant is used, the NPG melt is cooled by transfer of heat to the surrounding air and by heat radiation. Here, the term "coolant" refers to a fluid heat-transfer medium which is heated by thermal contact with the NPG and is cooled in another place. The plant components themselves, for example a cooling belt, are not included among "coolants".

The NPG particles are preferably packed at a temperature below 30° C.

According to the invention, the order of cooling, crystallization and comminution can be chosen at will. In general, the order is prescribed by the cooling apparatuses used.

In one embodiment of the invention, the NPG melt is firstly cooled and crystallized and then comminuted. For this purpose, at least the initial cooling is preferably carried out on a cooling belt or a flaking roll. These apparatuses are known per se.

In a further embodiment of the invention, the NPG melt is firstly comminuted and then cooled and crystallized. This can be achieved, for example, using a cooling belt or a pelletizing pan. In contrast to the above embodiment, this embodiment does not produce, when using a cooling belt, a continuous film of NPG on the cooling belt, but instead many droplets are dropped onto the cooling belt with the aid of droplet formers or similar devices.

When using the preferred cooling apparatuses described, cooling is, according to the present invention, firstly carried out slowly, as described above. This can be followed by rapid cooling in a known manner.

When cooling is carried out on a cooling belt, cooling can firstly be carried out without use of a coolant or with use of a coolant having a temperature in the range from 50 to 120° C. on a first region of the cooling belt, after which cooling is carried out with use of a coolant having a temperature of less than 40° C., in particular from 5 to 35° C. on a second region of the cooling belt.

The slow cooling is achieved, for example, by molten NPG (melting point: about 140° C.) being applied in the form of a continuous film to a cooling belt by means of a suitable application apparatus, for example an overflow weir. At this application point, the belt is not cooled at all or cooled only moderately. It is also possible to preheat the belt, for example by means of drum heating. This preheating is generally combined with the region of absent or moderate cooling. To achieve a greater thickness of the film, the cooling belt can be equipped with lateral barriers, for example of rubber or silicone. The film thickness when using a cooling belt is preferably from 1 to 10 mm, particularly preferably from 2 to 5 mm. The slow cooling to a temperature of less than 30° C. can be carried out exclusively on a cooling belt which is used for solidification of the melt. Here, the solid-solid phase transformation can occur entirely on the cooling belt. It is also possible to bring the solidified product, which is partly or fully in the high-temperature form, to a temperature below 30° C. in further heat exchangers. These heat exchangers are generally installed downstream of the cooling belt, the flaking roll or the pelletizing pan. Examples of suitable heat exchangers or cooling apparatuses are continuously or discontinuously supplied plate heat exchangers, cooling belts, cooling helix conveyors, cooled screw conveyors, shaft coolers with movable internals, pneumatic transport devices or combinations thereof.

Further cooling of the NPG particles can be carried out after dispensing into a storage or transport container. Such containers are, for example, sacks, tubs and similar containers. However, the product is preferably cooled sufficiently prior to dispensing into the storage or transport containers.

According to the present invention, the NPG particles can have any desired geometry. In general, the geometry is prescribed by the cooling apparatus and downstream or upstream dividing device used. The NPG particles are frequently in the form of flakes. However, they can also be in the form of droplets or pellets, or else in any other geometric forms. The pellet form is particularly effective in additionally countering caking of the product during storage.

The choice of the type of finished product (flakes, pellets, etc.) and the selection of one of the processes described for solidifying and cooling the NPG generally depends on the circumstances at the production site and on the wishes of the user. Inexpensive cooling is possible, in particular, by use of a single cooling belt which has different cooling zones and thus ensures slow cooling of the NPG melt.

The residence time of the NPG on the cooling belt, the flaking roll or the pelletizing pan is preferably from 0.1 to 20 minutes, particularly preferably from 2 to 15 minutes, in particular from 3 to 10 minutes.

The total residence time of the NPG in the apparatuses employed for cooling is preferably from 4 to 240 minutes, particularly preferably from 4 to 60 minutes.

The particle size of the NPG particles produced according to the present invention, characterized by the mass, is preferably from 0.05 g to 1 g. Here, as already described above, very different geometries of the individual NPG particles are possible. The geometry also depends on the particular field of application for the finished NPG.

The residence time on a belt cooler used alone for cooling is preferably from 4 to 20 minutes, particularly preferably from 4 to 10 minutes.

The invention is illustrated by the examples below.

EXAMPLES

Comparative Example C1

Molten NPG was applied at a temperature of 150° C. to a cooling belt having a width of 1.5 m and a length of 7 m by means of a ram apparatus. Owing to the low viscosity of the molten NPG, a continuous film was formed. The belt was cooled by cooling water having an admission temperature of about 10° C. At a feed rate of 500 kg of NPG melt per hour, flakes having a thickness of from 1 to 1.5 mm were obtained at the scraper. The product temperature at the scraper was 19° C. The scraped-off product was then packed in two sacks of 5 kg and 25 kg. The sacks were then stored at from 10 to 20° C. under a pressure of 0.5 metric ton/m$^2$ with exclusion of moisture. After six weeks, the sacks were opened and evaluated. The contents of both sacks were hard as rock: the flakes were completely caked.

Comparative Example C1 shows that caking is not attributable exclusively to the presence of the high-temperature form and its transformation during storage. Although the temperature was always less than 32° C. both when packing in sacks and also during storage, the product described tended to cake.

Example 1

Using the flaking apparatus described in the Comparative Example, liquid NPG was solidified in the manner described, but cooling with cooling water was omitted. Cooling thus occurred exclusively as a result of heat losses to the surroundings. The product scraped off by the scraper was soft and sticky, partly glassy and had a temperature of 50° C. 5 kg of this product were introduced into a plate heat exchanger. The spacing of the plates of the heat exchanger was 35 mm. The product was subsequently cooled for 60 minutes by means of a cooling water stream of 1 m$^3$/h at a temperature of 10° C. During this time, the product cooled from 49° C. to 27° C. The product was then taken from the heat exchanger, placed in a sack and stored as described in the Comparative Example. After 8 weeks the contents of the sack were examined. The product was completely free-flowing and showed not the slightest signs of caking.

Example 2

Molten NPG was applied via an overflow weir to a cooling belt having a length of 7 m. To preheat the belt, the back drum was heated to about 50° C. by means of hot water. The first four meters of the belt were not cooled, and the last three meters were cooled using cooling water having a temperature of 8° C. The residence time of the product on the belt was 4.5 minutes. The product was, at a temperature of 15° C., placed in a sack and stored as described above. After six weeks, the contents of the sack were examined. The product remained completely free-flowing and displayed no signs of caking.

Example 3

Molten NPG was applied in the form of droplets to the belt described in Example 2 by means of a droplet former. Elongated pellets having an area of 4 mm/6 mm and a thickness of 2 mm were obtained. Since cooling by means of cooling water was not employed, the product temperature at the scraper was 50° C. The product was allowed to stand overnight in a tub. Next morning, the product temperature was 25° C. The solid-solid phase transformation had proceeded to completion. After storage for eight weeks under the above-described conditions, the product was completely free-flowing and displayed no signs of caking.

We claim:

1. A process for finishing neopentyl glycol by cooling, crystallizing and comminuting a neopentyl glycol melt and subsequently packing the resulting neopentyl glycol particles in storage or transport containers, which comprises cooling the melt at the commencement of cooling for at least 1/10 minutes without use of a coolant or with the use of a coolant having a temperature in the range from 50 to 120° C. and packing the product at a temperature below 30° C.

2. A process as claimed in claim 1, wherein the neopentyl glycol melt is firstly cooled and crystallized and then comminuted.

3. A process as claimed in claim 2, wherein at least the initial cooling is carried out on a cooling belt or a flaking roll.

4. A process as claimed in claim 1, wherein the neopentyl glycol melt is firstly comminuted and then cooled and crystallized.

5. A process as claimed in claim 4, wherein at least the initial cooling is carried out on a cooling belt or a pelletizing pan.

6. A process as claimed in claim 1, wherein, when carrying out cooling on a cooling belt, cooling is carried out without use of a coolant or with use of a coolant having a temperature in the range from 50 to 120° C. on a first region of the cooling belt and cooling is carried out with use of a coolant having a temperature of less than 40° C. on a second region of the cooling belt.

7. A process as claimed in claim 3, wherein cooling to a temperature below 30° C. is achieved by means of further heat exchangers which are located downstream of the cooling belt, the flaking roll or the pelletizing pan.

8. A process as claimed in claim 3, wherein the residence time of the neopentyl glycol on the cooling belt, the flaking roll or the pelletizing pan is from 0.1 to 20 minutes.

9. A process as claimed in claim 1, wherein the total residence time of the neopentyl glycol in the apparatuses used for cooling is from 4 to 240 minutes.

* * * * *